US007425635B2

(12) United States Patent
Franklin et al.

(10) Patent No.: US 7,425,635 B2
(45) Date of Patent: *Sep. 16, 2008

(54) PRODRUGS AND CONJUGATES OF THIOL- AND SELENOL-CONTAINING COMPOUNDS AND METHODS OF USE THEREOF

(75) Inventors: Michael R. Franklin, Salt Lake City, UT (US); Jeanette Roberts, Monona, WI (US); Trek Aboul-Fadl, Assiut (EG)

(73) Assignee: University of Utah Research Foundation, Salt Lake City, UT (US)

( * ) Notice: Subject to any disclaimer, the term of this patent is extended or adjusted under 35 U.S.C. 154(b) by 114 days.

This patent is subject to a terminal disclaimer.

(21) Appl. No.: 11/033,464

(22) Filed: Jan. 11, 2005

(65) Prior Publication Data
US 2005/0267172 A1    Dec. 1, 2005

Related U.S. Application Data

(63) Continuation-in-part of application No. 10/051,463, filed on Jan. 18, 2002, now Pat. No. 6,841,536, which is a continuation of application No. 09/485,321, filed as application No. PCT/US98/16324 on Aug. 6, 1998, now Pat. No. 6,340,746.

(60) Provisional application No. 60/055,019, filed on Aug. 7, 1997.

(51) Int. Cl.
C07C 395/00    (2006.01)
C07D 293/00    (2006.01)
(52) U.S. Cl. ................................. 548/100; 562/899
(58) Field of Classification Search ............. 548/100; 514/92
See application file for complete search history.

(56) References Cited

U.S. PATENT DOCUMENTS

| 3,710,795 | A  | 1/1973  | Higuchi et al. ............... 424/424 |
| 4,011,221 | A  | 3/1977  | Sakakibara et al. .......... 260/252 |
| 4,617,189 | A  | 10/1986 | Stockel et al. ............... 424/162 |
| 4,868,114 | A  | 9/1989  | Nagasawa et al. ........... 435/112 |
| 5,578,470 | A  | 11/1996 | Kerkenaar et al. .......... 435/130 |
| 5,667,791 | A  | 9/1997  | Hersh et al. ................. 424/401 |
| 6,340,746 | B1 | 1/2002  | Roberts et al. .............. 536/17.4 |
| 6,841,536 | B2 | 1/2005  | Roberts et al. .............. 514/23 |

FOREIGN PATENT DOCUMENTS

| EP | 0 277 688 B1 | 10/1993 |
| WO | WO 91/02741  | 7/1991  |

OTHER PUBLICATIONS

Antonucci et al, Bulletin of Molecular Biology and Medicine, vol. 2(2), pp. 80-84, Jun. 1977, "Inhibition of Protein Synthesis in Rabbit Reticulocytes".*

Baran and Drabarek "Studies on Synthesis of S-Glycosidic Bond Between Cysteine and Glucose or Galactose." *Polish J. Chem.* 52:941-946 (1978).
Baruchel et al. "In vivo Selective Modulation of Tissue Glutathione in a Rat Mammary Carcinoma Model." *Biochem. Pharmacol* 50(9):1505-1508 (1995).
Bezlepkin et al. "The Prolongation of Survival in Mice by Dietary Antioxidants Depends on their Age by the Start of Feeding this Diet." *Mechanisms of Ageing and Development* 92:227-234 (1996).
Blot et al. "Nutrition Intervention Trials in Linxian, China: Supplementation with Specific Vitamin/Mineral Combinations, Cancer Incidence, and Disease-specific Mortality in the General Population." *J Natl Cancer Inst.* 85(18):1483-1492 (Sep. 15, 1993).
Bohm et al. "A Feasibility Study of Cisplatin Administration with Low-Volume Hydration and Glutathione Protecting in the Treatment of Ovarian Carcinoma." *Anticancer Res* 11:1613-1616 (1991).
Boucher et al. "Oral Selenium Supplementation in Rats Reduces Cardiac Toxicity of Adriamycin During Ischemia and Reperfusion." *Nutrition.* 11(5 Suppl):708-11 (Sep.-Oct. 1995).
Brock et al. "Serum Selenium Level in Relation to In situ Cervical Cancer in Australia." *J Natl Cancer Inst.* 83(4):292-3 (Feb. 20, 1991).
Carroll et al. "Efficacy of Radioprotective Agents in Preventing Small and Large Bowel Radiation Injury." *Dis Colon Rectum.* 38(7):716-722 (Jul. 1995).
Clark et al. "Selenium in Forage Crops and Cancer Mortality in U.S. Counties." *Arch Environ Health.* 46(1):37-42 (Jan.-Feb. 1991).
Clark et al. "Decreased Incidence of Prostate Cancer with Selenium Supplementation: Results of a Double-blind Cancer Prevention Trial." *Br J Urol.* 81(5):730-4 (May 1998).
Clark et al. "Effects of Selenium Supplementation for Cancer Prevention in Patients with Carcinoma of the Skin." *JAMA* 276(24):1957-1963 (1996).
Crary et al. "Potential Clinical Applications for High-Dose Nutritional Antioxidants." *Medical Hypotheses* 13:77-98 (1984).
Diamond et al. "The Inhibition of Radiation-induced Mutagenesis by the Combined Effects of Selenium and the Aminothiol WR-1065." *Mutat Res.* 356(2):147-54 (Sep. 23, 1996).

(Continued)

*Primary Examiner*—Elli Peselev
(74) *Attorney, Agent, or Firm*—Ballard Spahr Andrews & Ingersoll, LLP

(57) ABSTRACT

Disclosed are compounds having the formula

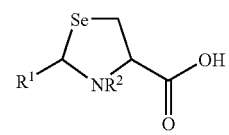

wherein $R^1$ is hydrogen, an alkyl group, an aryl group, a cycloalkyl group, an alkenyl group, an alkynyl group, an aralkyl group, or =O, $R^2$ is an alkyl group, an aryl group, a cycloalkyl group, an alkenyl group, an alkynyl group, or an aralkyl group, or the pharmaceutically acceptable salt or ester thereof. Also disclosed are methods of using the compounds.

2 Claims, No Drawings

OTHER PUBLICATIONS

Dorr, Robert "Chemoprotectants for Cancer Chemotherapy." *Seminars in Oncology* 18(1): Suppl 2:48-58 (1991).

Draguet and Renson "Synthese de la Selenazolidine, de N-Alcoylselenazolidines et de Leurs Derives de Substitution en 2 Bull." *Soc. Chim. Belges* 81:279-287 (1972).

El-Bayoumy et al. "Chemoprevention of Cancer by Organoselenium Compounds." *J. Cell. Biochem.* Supplement 22:92-100. (1995).

Goitein et al. "Future Prospects in Planning Radiation Therapy." *Cancer* 55(9 Suppl):2234-9 (1985).

Hildesheim et al. "Etude de L'inhibitond'une t-ARN $N_2$-guanin methyl transferase de foie de lapin par des analogues de la S-adensoyl homocyseine." *Biochimie* 1972;54:989-995 (May 1, 1985).

Institute of Medicine, Food and Nutrition Board. Dietary Reference Intakes: Vitamin C, Vitamin E, Selenium, and Carotenoids. National Academy Press, Washington, DC, 2000.

Ip et al. "In vitro and In vivo Studies of Methylseleninic Acid: Evidence that a Monomethylated Selenium Metabolite is Critical for Cancer Chemoprevention." *Cancer Res.* 60(11):2882-6 (Jun. 1, 2000).

Johansen et al. "Relationship Between the in vitro Radiosensitivity of Skin Fibroblasts and the Expression of Subcutaneous Fibrosis, Telangiectasia, and Skin Erythema After Radiotherapy," *Radiother Oncol.* 40(2):101-9 (Aug. 1996).

Käsbeck and Kessler "Synthesis of S-α-D-Glucosylated L-Cysteine—A Novel S-Glycosyl Amino Acid." *Liebigs Ann/Recueil* 165-167 (1997).

Knizhnikov et al. "The Effect of Dietary Levels of Selenium on Radiation Resistance . . . " *Nutrition Research* 16 (3): 505-516 (1996).

Konstantinov et al. "Antitumor, Nephrotoxic and Clastongenic Effect of cis-DDP with DDTC or NAC." *Neoplasma* 41(5):253-258 (1994).

Kumar et al. "Radioprotection by Antioxidant Enzymes and Enzyme Mimetics" *Pharmac. Ther.* 39:309-309 (1998).

Lautermann et al. "Glutathione Protection against Gentamicin Ototoxicity Depends on Nutritional Status." *Hearing Research* 86:15-24 (1995).

Leyck and Parnham "Acute Antiinflammatory and Gastric Effects of the Seleno-organic Compound Ebselen." *Agents Actions.* Jun.;30(3-4):426-31 (1990).

Li et al. "Charateritics of Selenazolidine Prodrugs of Selenocysteine: Toxicity, Selenium Levels, and Gluthaion Peroxidase Induction in A/J Mice." *Life Sciences* 75:447-459 (2004).

Li et al. "Chemoprotective Activity of Selenocystein Prodrugs Against the Tobacco Derived Nitrosamine NNK in the A/J Mouse Lung." Univ. Wisconsin.

Micke O, et al. "Selenium in the Treatment of Radiation-associated Secondary Lymphedema." *Int J Radiat Oncol Biol Phys.* 56(1):40-9 (May 1, 2003).

Monsigny et al. "Synthèse d'un nouveau type de glycoconjuguèLe thio-β-D-glucopyranoside de la L-cystèine." *Carbohydrate Res.* 59:589-593 (1997).

Nagasawa et al. "Prodrugs of L-Cysteine as Liver-Protective Agents, 2(RS)-Methylthiazolidine4R-Carboxylic Acid, a Latent Cysteine." *J. Med. Chem.* 25(5):489-491 (1982).

Niemierko and Goitein "Modeling of Normal Tissue Response to Radiation: The Critical Volume Model." *Int J Radiat Oncol Biol Phys.* 25(1):135-45 (Jan. 1993).

Reddy et al. "Evaluation of Organoselenium Compounds for Potential Chemopreventive Properties in Colon Cancer." *Anticancer Res.* 16(3A):1123-7 (May-Jun. 1996).

*Remington's Pharmaceutical Sciences*, latest edition, by E.W. Martin Mack Pub. Co., Easton, PA.

Roberts and Francetic "Chemoprotection Against Cyclophosphamide-induced Urotoxicity: Ribose-Cysteine." *Anticancer Res.* 14:383-388 (1994).

Roberts and Francetic "Mechanisms of Chemoprotection by Ribcys, a Thiazolidine Prodrug of L-Cysteine." *Med. Chem. Res.* 1:213-219 (1991).

Roberts and Francetic. "Time Course for the Elevation of Gluthahione in Numerous Organs of L1210-Bearing CDF1 Mice Given the L-Cytseine Prodrug, RibCys." *Toxicology Letters* 59:245-251 (1991).

Roberts et al. "Chemoprotection Against Cyclophosphamide-induced Urotoxicity: Comparison of Nine Thoil Protective Agents." *Anticancer Res.* 14:389-396 (1994).

Roberts et al. "Differential Chemoprotection Against Acetaminophen-Induced Hepatotoxicity by Latentiated L-Cysteines." *Chem. Res. Toxicol.* (Sep. 1998).

Roberts et al. "L-cysteine Prodrug Protects against Cyclophosphamide Urotoxicity Without Comprising Therapeutic Activity." *Cancer Chemther. Pharmacol.* 28:166-170 (1991).

Roberts et al. "Prodrugs of L-Cysteine as Protective Agents Against Acetaminophen-induced Hepatotoxicity. 2—(Polyhydroxyalkyl)- and 2-(polyacetoxyalkyl)thiazolidine-4(R) -carboxylic acids." *J. of Med. Chem.* 30:1891-1896 (1987).

Roberts et al. "Thiazolidine Prodrugs of Cycteamine and Cysteine as Radioprotective Agents." *Rad. Res.* 143:203-213 (1995).

Rowe et al. "Protective Effect of RibCys Following High-dose Irradiation of the Rectosigmoid." 36(7):681-687 (1992).

Schneider and Geyer, Hans-Ulrich "Verknüpfung von Zuckern mit Aminosäureestern lipophiler Alkohole zu grenzflächenaktiven Zuckerderivaten" Bd 330;182-187 (1963).

Schrauzer, G. "Selenium: Mechanistic Aspects of Anticarcinogenic Action." *Biol Trace Elem Res.* 33:51-62 (Apr.-Jun. 1992).

Sieja and Talerczyk. "Selenium as an Element in the Treatment of Ovarian Cancer in Women Receiving Chemotherapy." *Gynecol Oncol.* 93(2):320-7 (May 2004).

Stapleton "Selenium: an Insulin-mimetic." *Cell Mol Life Sci.* 57(13-14):1874-9 (Dec. 2000).

Steare and Yellon "The Potential for Endogenous Myocardial Antioxidants to Protect the Mycocardium Against Ischaemia-Reperfusion Injury: Refreshing the Parts Exogenous Antioxidants Cannot Reach?" *J. Mol. Cell. Cardiol.* 27:65-74 (1995).

Tamba "Role of Thiols in Radioprotection: Radiation Chemical Aspects." *J Biosci.* 44c:857-862 (1989).

Tanaka et al. "WS1279, A Novel Lipopeptide Isolated from *Steptomyces willmorei* Biological Activities." *J. Antibiotics* 46(11):1699-1706 (1993).

Taylor et al. "Prevention of Esophageal Cancer: The Nutrition Intervention Trials in Linxian, China. Linxian Nutrition Intervention Trials Study Group." *Cancer Res.* 54(7 Suppl):2029s-2031s Apr. 1, 1994).

Warters et al. "Modulation of Radiation-induced Apoptosis by Thiolamines." *Int. J. Radiat Biol.* 72(4):439-448 (1997).

Waters et al. "Antimutagenicity Profiles for Some Model Compounds." *Mutation Res.* 238:57-85 (1990).

Wiess and Landauer "Protection Against Ionizing Radiation by Antioxidant Nutrients and Phytochemicals." *Toxicology.* 189(1-2):1-20 (Jul. 15, 2003).

Yarbo et al. "Recent Advances in Cancer patient Management" *Sem. Oncol* 18(1):48-58, Supp. 2 (1991).

Yin, Cai et al. "Biochemical and Morphological Changes in the Lenses of Selenium and/or Vitamin E Deficient Rats." *Biomedical and Environ. Sci.* 7:109-115 (1994).

Yoshizawa et al. "Study of Prediagnostic Selenium Level in Toenails and the Risk of Advanced Prostate Cancer." *J Natl Cancer Inst.* 90(16):1219-24 (Aug. 19, 1998).

Yu et al. "A Preliminary Report on the Intervention Trials of Primary Liver Cancer in High-Risk Populations with Nutritional Supplementation of Selenium in China." *Biol Trace Elem Res.* 29(3):289-94 (Jun. 1991).

El-Sayed et al., "Acute effects of novel selenazolidines on murine chemoprotective enzymes," *Chemico-Bio. Interact.* 162:31-42 (2006).

El-Sayed et al., "Effect of selenium-containing compounds on hepatic chemoprotective enzymes in mice." *Toxicology* 220:179-188 (2006).

El-Sayed et al., Hepatic chemoprotective enzyme responses to 2-substituted selenazolidine-4(R)-Carboxylic acids, *J. Biochem. Mol. Toxic.* 20(6):292-301 (2006).

El-Sayed et al., "Murine hepatoma (Hepa1c1c7) cells: A responsive in vitro system for chemoprotective enzyme induction by organoselenium compounds," *Toxicology in Vitro* 21:157-164 (2007).

El-Sayed et al., "The antimutagenicity of 2-substitued selenazolidine-4-(R)-carboxylic acids," *Mutation Res.* 627(2):136-145 (2007).

Short et al., "Characteristics of selenazolidine prodrugs of selenocysteine: Toxicity and glutathione peroxidase induction in V79 cells," *J. Med. Chem.* 46:3308-3313 (2003).

Xie et al., "Selenazolidines as novel organoselenium delivery agents," *Bioorgan. Med. Chem. Letters* 11:2911-2915 (2001).

* cited by examiner

PRODRUGS AND CONJUGATES OF THIOL- AND SELENOL-CONTAINING COMPOUNDS AND METHODS OF USE THEREOF

RELATED APPLICATIONS

This application is a continuation-in-part of U.S. patent application Ser. No. 10/051,463 (now U.S. Pat. No. 6,841, 536), titled "PRODRUGS AND CONJUGATES OF THIOL- AND SELENOL-CONTATNING COMPOUNDS AND METHODS OF USE THEREOF," filed Jan. 18, 2002 and issued Jan. 11, 2005, which is a continuation of U.S. patent application No. 09/485,321 filed Jul. 20, 2000, (now U.S. Pat. No. 6,340,746) which was nationalized from PCT/US98/ 16324 filed Aug. 6, 1998 and issued on Jan. 22, 2002, which claimed priority to U.S. Provisional Patent Application Ser. No. 60/055,019, filed Aug. 7, 1997 (which applications are hereby incorporated by reference).

This invention was made with government support under grant number GM058913-05 awarded by the National Institutes of Health. The Government has certain rights to this invention.

FIELD OF THE INVENTION

The present invention relates to sulfur- and selenium-containing compounds and methods for using these compounds to protect mammals from toxic insults. More specifically, the present invention relates to prodrugs and conjugates of thiol- or selenol-containing compounds, such as cysteine, cysteamine, glutathione, selenocysteine, selenocysteamine, and the Walter Reed (WR) compounds.

BACKGROUND OF THE INVENTION

Technical Background

Thiol- or selenol-containing compounds, e.g., cysteine, cysteamine, glutathione, selenocysteine, selenocysteamine, and the WR compounds, are known protective and preventive agents. Potential protective or preventive uses of such agents are widespread, as in reducing the unwanted side effects of chemo- or radiotherapy of cancer, improving cardiovascular function, preventing mutagenesis, preventing the initiation and/or progression of cancer, reducing toxic consequences of planned or unplanned radiation or chemical exposures, slowing the aging process, and preventing cataract formation. New evidence also links these compounds to altered gene expression and enhanced cellular repair processes.

The activity of these thiol- or selenol-containing compounds is mainly due to the sulfur or selenium atom participating in nucleophilic attack on toxic electrophiles, scavenging free radicals, effecting repair of damaged targets through hydrogen atom donation, altering the redox status of the cell, or affecting gene transcription or protein function.

For example, the reduced form of glutathione (Glu-Cys-Gly), a naturally occurring tripeptide with a free sulfhydryl group (SH), serves as a sulfhydryl buffer that maintains the cysteine residues of hemoglobin and other proteins in a reduced state. Glutathione also plays a key role in detoxifying the body by reacting with both endogenous and exogenous compounds, such as hydrogen peroxide and other peroxides.

Evidence suggests that glutathione is useful at protecting the body from the harmful side effects of radiation and chemotherapy that often accompany cancer treatment. Cyclophosphamide (CTX), for example, is a widely used antitumor agent whose clinical utility is limited by its bladder toxicity. During CTX metabolism in the body, a compound, acrolein, is released. Acrolein is thought to be responsible for the urotoxicity of CTX. Glutathione has been implicated in CTX detoxification by conjugating to acrolein.

It has been of significant interest in the art, therefore, to increase glutathione synthesis especially during periods of toxic insults and maintain good levels of glutathione in the subject. L-cysteine, a reactant in normal glutathione biosynthesis, is known to increase the synthesis of endogenous glutathione. To date, a significant challenge in the art has been to provide L-cysteine to cells at sufficiently high levels to drive glutathione biosynthesis and maintain healthy levels. As disclosed, for example, in U.S. Pat. No. 4,868,114 to Nagasawa et al., prodrugs of L-cysteine (i.e., chemical compounds converted to L-cysteine in the cell), such as RibCys, can be used by the cell to drive glutathione biosynthesis shown below.

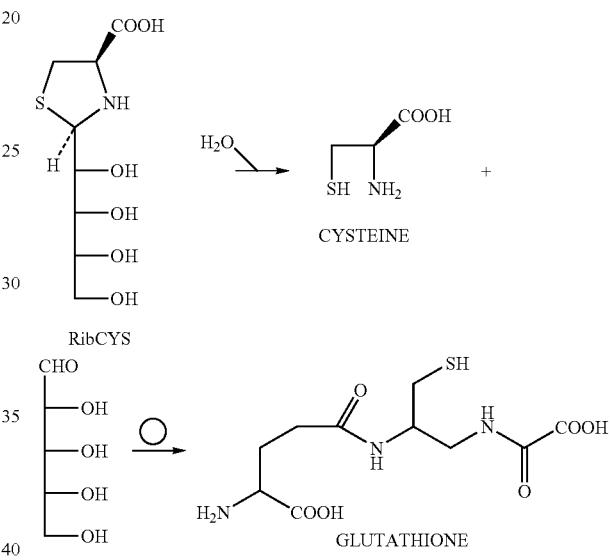

These prodrugs have been shown to offer good protection against a variety of toxic insults. However, the initial prodrugs are highly water soluble and are rapidly excreted by the body.

WR compounds are also of significant interest in the art. Over 4400 WR compounds were prepared and tested at the Walter Reed Army Hospital after World War II in an effort to develop radioprotective compounds that might be employed by military personnel during a nuclear encounter. The single agent with the greatest potential that arose from that extensive effort was WR-2721, which is converted to WR-1065 by enzymatic cleavage. These compounds have several shortcomings, however, including that they possess noteworthy toxicity and little oral activity, greatly reducing their clinical utility.

Finally, selenocysteine is of significant interest in the art for its antioxidant and anticancer properties. In fact, selenium has received significant attention for its ability to inhibit or delay the onset of AIDS caused by HIV infection. Selenium is also a cofactor of glutathione peroxidase, an enzyme which has been implicated in many detoxifying processes.

Selenium is an essential mineral that is critical to the normal functioning of many species, including humans. It also has demonstrated activity as a cancer chemopreventive agent. Selenium-containing compounds appear to have especially high preventive activity against the initiation phase of colorectal cancer, although its chemoprotective ability has been extended to cancers in many organs, caused by a variety of carcinogens.

To achieve this chemopreventive activity, levels of selenium at least five-fold greater than that required for normal nutritional status appear to be necessary. In addition, selenium must be given continuously for maximum inhibition. Unfortunately, selenium is also known for its profound toxicity, making selenium supplementation a distinct challenge.

Current selenium supplements rely on inorganic forms, such as sodium selenite ($Na_2SeO_3$) or sodium selenate ($Na_2SeO_4$). While these forms have some value, they are considered more toxic than necessary, and are unlikely to be useful in cancer chemoprevention. Several organoselenium compounds, which appear to be less toxic in general than the inorganic forms, have been proposed for in vivo use, but the full potential of this strategy has not yet been realized. In general, however, it is very clear that the chemical form in which selenium is introduced consistently shows a marked influence on biological outcomes, including cancer chemoprevention and toxicity.

Selenocysteine is an organic form that is present in the body and is now recognized as the 21st amino acid used in protein synthesis. While it represents a valuable biochemical form, selenocysteine is chemically unstable and difficult to handle, which has undoubtedly deterred its study and use. In addition, even though it possesses greatly reduced inherent toxicity, it still may be too toxic at chemopreventive doses to the therapeutically useful. Accordingly, prodrug forms of selenocysteine that possess reduced inherent toxicity and improved physicochemical properties would be desirable.

Objects of the Invention

It is, therefore, an object of the invention to provide prodrugs and conjugates of thiol- or selenol-containing compounds, such as cysteine, cysteamine, glutathione, selenocysteine, selenocysteamine, and the WR compounds.

Another object of the invention is to provide such thiol- or selenol-containing compounds displaying reduced toxicity and increased clinical utility.

Another object of the invention is to provide such thiol- or selenol-containing compounds with increased lipophilicity that can target a specific organ or region of the body.

Another object of the invention is to provide such thiol- or selenol-containing compounds that can be conjugated to antioxidants, such as vitamin C and E, thus maximizing the effects by providing different agents that work by complementary mechanisms.

Further objects of the invention will become evident in the description below.

BRIEF SUMMARY OF THE INVENTION

The present invention is directed to novel prodrugs and conjugates of thiol- or selenol-containing compounds, including cysteine, cysteamine, glutathione, selenocysteine, selenocysteamine, and the WR compounds. Potential protective or preventive uses of such agents are widespread, as in reducing the unwanted side effects of chemo- or radiotherapy of cancer, improving cardiovascular function, preventing mutagenesis, preventing the initiation and/or progression of cancer, reducing toxic consequences of planned or unplanned radiation or chemical exposures, slowing the aging process, preventing cataract formation, etc.

Prodrugs are inactive forms of a parent drug that have been created to overcome one or more barriers to their effective use. In the present invention, prodrugs have been designed to overcome the chemical instability and/or possible toxicity barriers that exist with the parent drug.

In one embodiment, the invention relates to the design, synthesis, and evaluation of prodrugs of L-cysteine and L-selenocysteine, containing a thioglycoside or selenoglycoside on the free thiol or selenol. The protecting group will, in addition to protecting the thiol or selenol from oxidation, permit the targeting of specific sites within the body.

For example, the galactose protected cysteine shown below will target the liver and will enter the cytoplasm of hepatocytes. Delivering L-cysteine to hepatocytes has numerous uses, including protection against hepatotoxins, such as acetaminophen, and against side effects caused by local radiation treatments.

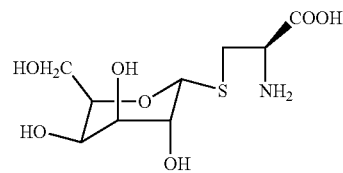

The cysteine/selenocysteine prodrugs can be depicted by the formula:

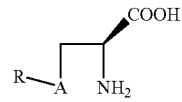

where A is a sulfur or a selenium, and R is derived from a mono- di- or oligo-saccharide, such as ribose, galactose, glucose, or mannose.

A second embodiment relates to the design, synthesis, and evaluation of novel prodrugs that are derivatives of cysteamines or selenocysteamines, such as of WR compounds, particularly WR-1065. The prodrug strategy is similar to that employed for L-cysteine, using a protecting group R'. R' is typically a sugar, such as ribose. The modified WR prodrugs have numerous uses including protection against the side effects of radiation and chemotherapy, radiation and chemical induced mutations, such as from exposure to radiation during a nuclear accident or chemical spill, and even spontaneous mutations which are the cause of most cancers.

These prodrugs can be described by the formulas:

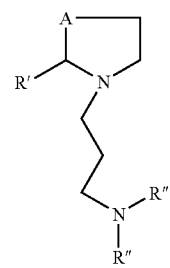

where A is sulfur or selenium, R' is derived from a sugar and has the formula $(CHOH)_nCH_2OH$, where n is 1 to 5. R' may also be hydrogen, an alkyl or aryl group, such as methyl, ethyl, benzyl, carboxyl, polyhydroxyalkyl, or phenyl, or may also be =O. The R" groups may be the same or different and may be alkyl, alkoxy, carboxy, such as acetyl, methyl or ethyl.

These novel thio- and selenol-containing compounds overcome several problems facing the art, including toxicity, water-solubility, and lack of target specificity. First, the protective or preventive activity and clinical utility will be greatly enhanced by converting the cysteine, cysteamine, glutathione, selenocysteine, selenocysteamine, and WR compounds to thiazolidine and selenazolidine prodrug forms. These prodrugs provide a slow release form of the thiol-/selenol-amine, which greatly reduces observed toxicity (with related compounds), but provides the active agent after enzymatic or non-enzymatic biotransformation In a third embodiment, the invention relates to the design, synthesis, and evaluation of novel covalent conjugates of thiolamines or selenolamines and antioxidant vitamins, e.g., Vitamin E and Vitamin C. These compounds include conjugates of any of the prodrug compounds of the invention defined above conjugated with Vitamin C or Vitamin E. Also contemplated by the invention are conjugates of antioxidant vitamins with the following thiol- and selenol-amines and derivatives thereof; cysteine, cystine, cysteamine, cystamine, glutathione, selenocysteine, selenocysteamine, selenocystine, selenocystamine, and WR compounds (WR-1065 and WR-33278).

An example, shown below is a conjugate of cysteamine and Vitamin C.

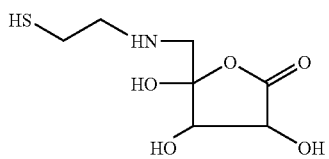

These compounds are effective because protective or preventive treatment of toxic insults will be far more effective if thiol- or selenol-containing compounds are delivered together with antioxidants such as vitamin C and E which also play a protective and preventive action in the body. The complementary mechanisms of these compounds would increase the overall effectiveness of treatment.

In yet another embodiment, the invention relates to the design, synthesis, and evaluation of novel L-cysteine prodrugs which have been modified with ester or amine groups at the carboxylic acid position. These can be described by formula;

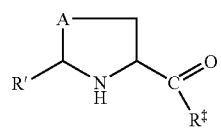

where A is sulfur or selenium, and R' is derived from a sugar and has the formula $(CHOH)_nCH_2OH$, where n is 1 to 5. R' may also be an alkyl or aryl group, such as methyl, ethyl, benzyl, carboxyl, or phenyl, or may also be =O. $R^\ddagger$ is an axlkoxy, such as —$OR^1$ where $R^1$ is ethyl, methyl. $R^\ddagger$ may also be an amine group (—$NR^\dagger_2$) where the $R^\dagger$ groups are the same or different and hydrogen or an alkyl group, such as methyl.

Yet another embodiment of the invention is the condensation product of a selenolamine and a carbonyl donor characterized by the formula:

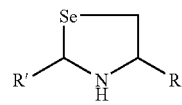

where R is COOH (prodrug of L-selenocysteine) or is H (prodrug of selenocysteamine). R' is derived from a sugar and has the structure $(CHOH)_nCH_2OH$, and where n is 1 to 5; an alkyl or aryl group, such as methyl, ethyl, benzyl, phenyl or carboxyl; or =O.

In another embodiment, described herein are compounds having the formula

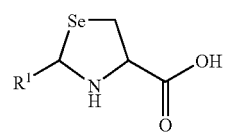

wherein $R^1$ is hydrogen, an alkyl group, and aryl group, a cycloalkyl group, an alkenyl group, an alkynyl group, an aralkyl group, or =O, or the pharmaceutically acceptable salt or ester thereof.

In a further aspect, described herein are compounds having the formula

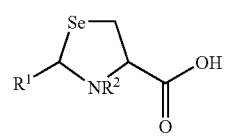

wherein $R^1$ is hydrogen, an alkyl group, an aryl group, a cycloalkyl group, an alkenyl group, an alkynyl group, an aralkyl group, or =O, $R^2$ is an alkyl group, an aryl group, a cycloalkyl group, an alkenyl group, an alkynyl group, or an aralkyl group, or the pharmaceutically acceptable salt or ester thereof. Also disclosed are methods of using the compounds.

Disclosed herein are methods for reducing toxicity of a substance in a mammal, comprising administering the compounds disclosed herein to the mammal.

Also disclosed are methods of reducing unwanted side effects of radiotherapy of cancer in a mammal comprising administering the compounds disclosed herein to the mammal.

Also disclosed are methods of reducing unwanted side effects of chemotherapy of cancer in a mammal comprising administering the compounds disclosed herein to the mammal.

Also disclosed are methods of improving cardiovascular function in a mammal comprising administering the compounds disclosed herein to the mammal.

Further disclosed are methods of preventing mutagenesis in a mammal comprising administering the compounds disclosed herein to the mammal.

Also disclosed are methods of preventing the initiation and/or progression of cancer in a mammal comprising administering the compounds disclosed herein to the mammal.

Further disclosed are methods of treating cancer in a mammal comprising administering the compounds disclosed herein to the mammal. The radiation can be planned or unplanned.

Also disclosed are methods of reducing toxic consequences of radiation in a mammal comprising administering the compounds disclosed herein to the mammal.

Further disclosed are methods of slowing affects of aging in a mammal comprising administering the compounds disclosed herein to the mammal.

Also disclosed are methods of preventing cataract formation in a mammal comprising administering the compounds disclosed herein to the mammal.

Also disclosed are methods of treating cataract formation in a mammal comprising administering the compounds disclosed herein to the mammal.

Also disclosed are methods of treating diabetes in a mammal comprising administering the compounds disclosed herein to the mammal.

Also disclosed are methods of treating inflammation in a mammal comprising administering the compounds disclosed herein to the mammal.

DETAILED DESCRIPTION OF THE INVENTION

I. Definitions

The present invention may be understood more readily by reference to the following detailed description of preferred embodiments of the invention and the Examples included therein and to the Figures and their previous and following description. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates," or "elevation" refer to increases above basal levels, e.g., as compared to a control. The terms "low," "lower," "reduces," or "reduction" refer to decreases below basal levels, e.g., as compared to a control. For example, basal levels are normal in vivo levels prior to, or in the absence of, inflammation or the addition of an agent which causes inflammation.

"Toxicity" is defined as an abnormal accumulation of toxic substances in a subject. "Toxicity" is synonymous with "toxic insult." A number of criteria can be used to assess the clinical significance of toxicity data: (a) type/severity of injury, (b) reversibility, (c) mechanism of toxicity, (d) interspecies differences, (e) availability of sensitive biomarkers of toxicity, (e) safety margin (non toxic dose/pharmacologically active dose), and (f) therapeutic potential.

"Cancer therapy" is defined as any treatment or therapy useful in preventing, treating, or ameliorating the symptoms associated with cancer. Cancer therapy can include, but is not limited to, apoptosis induction, radiation therapy, and chemotherapy.

A weight percent of a component, unless specifically stated to the contrary, is based on the total weight of the formulation or composition in which the component is included.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "alkenyl group" is defined as a branched or unbranched hydrocarbon group of 2 to 24 carbon atoms and structural formula containing at least one carbon-carbon double bond.

The term "alkynyl group" is defined as a branched or unbranched hydrocarbon group of 2 to 24 carbon atoms and a structural formula containing at least one carbon-carbon triple bond.

The term "aralkyl" as used herein is an aryl group having an alkyl, alkynyl, or alkenyl group as defined above attached to an aryl group. An example of an aralkyl group is a benzyl group.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

Any of the compounds described herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like.

In another aspect, if the compound possesses a basic group, it can be protonated with an acid such as, for example, HCl or $H_2SO_4$, to produce the cationic salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a salt.

Ester derivatives are typically prepared as precursors to the acid form of the compounds and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

It is contemplated that the pharmaceutically-acceptable salts or esters of the compounds described herein can be used as prodrugs or precursors to the active compound prior to the administration. For example, if the active compound is unstable, it can be prepared as its salts form in order to increase stability. Prior to administration, the salt can be converted to the active form. For example, the salt can be added to a saline solution to produce the active compound, followed by administration of the saline solution containing the active compound to the subject.

II. Thioglycoside Prodrugs

1. Agent Design

Prodrugs of L-cysteine and L-selenocysteine containing a thioglyco side or selenoglycoside on the free thiol or selenol can be prepared. The protecting group will, in addition to protecting the thiol or selenol from oxidation, permit the targeting of specific sites within the body.

For example, a galactose protected cysteine will target the liver and will enter the cytoplasm of hepatocytes. Delivering L-cysteine to hepatocytes has numerous uses, including protection against hepatotoxins, such as acetaminophen, and against side effects caused by local radiation treatments.

2. Chemical Synthesis

The prodrug of L-cysteine (compound 1) was prepared as shown in Scheme 1. The protected thiogalactose analog 2 was alkylated with L-serine Θ-lactone 3 in the presence of potassium carbonate. The protected thiopyranoside 4 was isolated in 70% yield after purification by silica gel chromatography. The acetate protecting groups were removed by treatment of 4 with methanolic ammonia, giving 5. Sodium in liquid ammonia was then used to remove the amino protecting groups, giving the target prodrug 1.

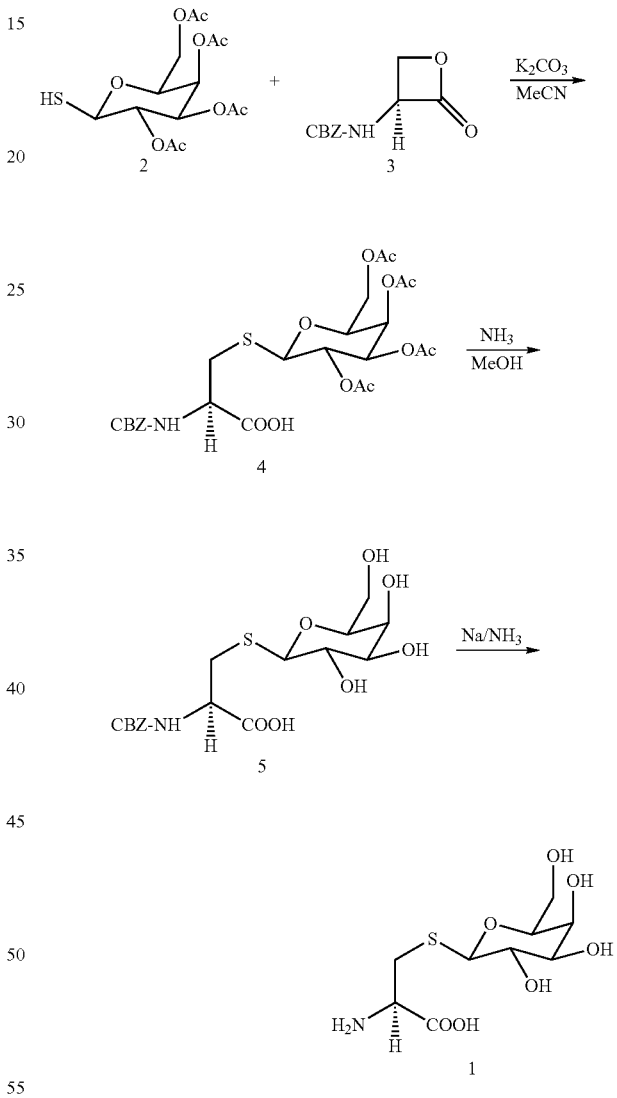

Scheme I

An alternative route to prodrug 1 features the formation of the thiopyranoside bond by displacement of iodine from a suitably protected galactosyl iodide (Scheme II). This route would eliminate the need to prepare Θ-lactone 3 (the purification of which is difficult and not very versatile with respect to the range of I-amino protecting groups that can be used) and makes it possible to use hydroxyl (on the sugar) and amino (on the cysteine) protecting groups that can be removed in a single reaction to generate the target compound 1.

Scheme II

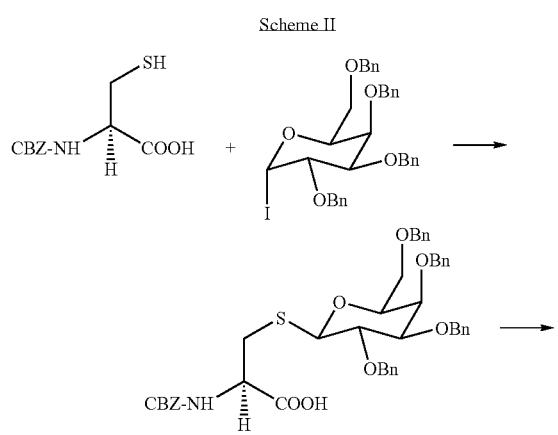

II. Thiazolidine Prodrugs of Walter Reed (WR) Compounds

1. Agent Design

Thiazolidine prodrug forms can be prepared from the thiolamine and virtually any carbonyl-containing compound, particularly the sugars, such as aldose monosaccharide, D-ribose, as an aldehyde that results in thiazolidines with superior protective activity. Numerous sugars or alkyl/aryl aldehydes or ketones can be used. These product thiazolidines will undergo non-enzymatic dissociation to liberate the active thiolamine. In addition, the 2-oxo derivatives can be prepared, which require enzymatic action to liberate the active thiolamine.

2. Chemical Synthesis a. 2-Thiazolidinone (prodrug of cysteamine and starting material for other syntheses) Carbonyl diimidazole (15.75 g 0.097 mol) was dissolved, with heating, in 150 ml acetonitrile, which has been degassed and flushed with nitrogen. To this was added, cysteamine hydrochloride (10.01 g, 0.088 mol), potassium carbonate (13.50 g, 0.098 mol), and 18-crown-6 (catalytic amount), and the solution was stirred at reflux (~80° C.) for 19 hours. After this time, solvent was removed in vacuo. The crude product was redissolved in 100 ml 5% sodium carbonate and refluxed for 1 hour, then acidified to pH 2 with concentrated hydrochloric acid. The resulting solid was removed via filtration and the product was extracted from the filtrate into ethyl acetate (12×35 ml). The combined organic portion was washed with 1 M potassium chloride and saturated sodium chloride (50 ml each), dried over sodium sulfate, filtered, and dried in vacuo. Yield was 3.8 g, 42%.

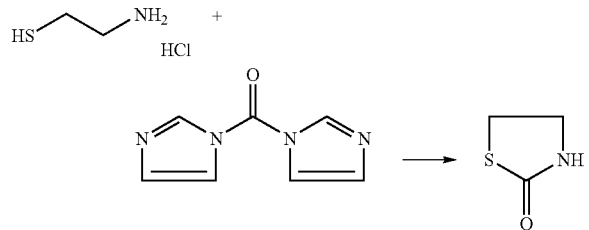

b. (N',N'-Dimethyl-3-aminopropyl)-2-thiazolidinone

To a solution of 2-thiazolidinone (4.15 g, 40.18 mmol) in acetonitrile (60 ml) were added potassium carbonate (13.3 g 96.2 mmol), N,N-dimethyl-3-aminopropyl chloride hydrochloride (7.63 g, 48.3 mmol), and 18-crown-6 (catalytic amount). The mixture was refluxed for 18 hours, solvent removed in vacuo, then redissolved in dichloromethane and 1 M potassium chloride (40 ml each). The aqueous phase was isolated and extracted twice with 30 ml portions of dichloromethane. The combined organic fraction was washed with saturated sodium chloride (~50 ml), dried over sodium sulfate, filtered, and dried in vacuo. The crude product was purified via silica gel chromatography, using a 10:1 ratio of silica gel A, 200-425 mesh, and eluting with 5% methanol in chloroform, yielding 1.15 g (15%) pure product.

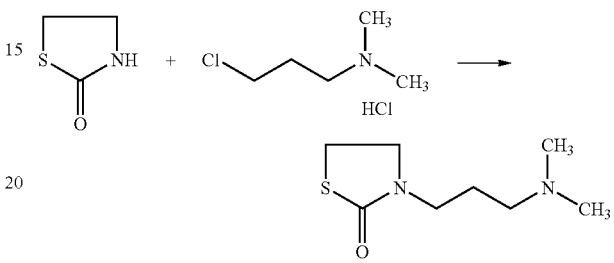

c. 3-(3-Aminopropyl)-2-thiazolidinone

To a solution of 2-thiazolidinone (0.994 g, 9.64 mmol) in acetonitrile (10 ml) were added N-phthalimido-3-bromopropylamine (2.88 g, 10.7 mmol), potassium carbonate (1.64 g, 11.9 mmol), and 18-crown-6 (catalytic amount). The mixture was refluxed about 17 hours, solvent was removed in vacuo, and the resulting solid was redissolved in 1 M potassium chloride and dichloromethane (~25 ml each). The aqueous phase was separated and extracted with 2×25 ml dichloromethane. The combined organic fraction was dried over sodium sulfate, filtered, and dried in vacuo. The crude product was recrystallized from acetone/methanol to give 1.54 g (55% yield). To a warmed solution of the phthalimido protected amine (1.53 g, 5.27 mmol) in 6:1 isopropanol:water was added sodium borohydride (1.01 g, 26.7 mmol), and the mixture was stirred at 60° C. for 22 hours. Glacial acetic acid (5.4 ml) was added, and the solution was stirred at 80° C. for 2 hours, then the solution was cooled and dried in vacuo. The product was redissolved in 6 N hydrochloric acid, washed with ether (2×30 ml), then dried in vacuo. The product was purified via recrystallization from hot water.

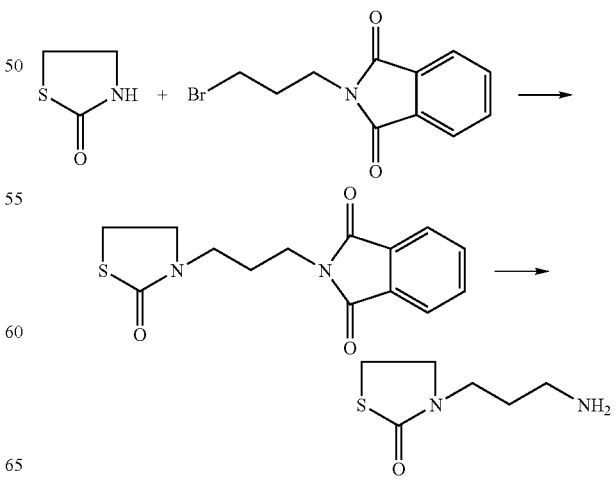

Similar procedures are employed to produce the terminal monomethylated form, as well as the terminal N-acetyl compound. In addition, various allyl or aryl aldehydes or ketones are employed to produce the corresponding allyl or aryl substituent at the 2 position, as opposed to the 2-oxo derivatives presented above.

Radioprotection in *E. coli* AB1157

A well characterized bacterial system was used as an initial screen for radioprotective activity of the novel compounds. A single colony of the bacteria, growing on a plate of LB medium (10 g tryptone, 5 g yeast extract, plus 5 g NaCl in 1 L water), was inoculated into 2 mL LB and incubated overnight. 20 mL LB medium were then inoculated with 600 μL of the overnight culture, and incubated with shaking at 37° C., 250 rpm. The cells were collected and washed with phosphate buffered saline. At this point the bacteria could be irradiated, treated with drug, etc., as outlined below. After dilution of the treated cells to 100 cells per 100 μL, they are plated out and incubated overnight. Cell viability is then measured by colony forming ability.

calculated. The positive controls homocysteine thiolactone (HCTL) and WR-1065 showed the greatest amount of protection.

III. Covalent Conjugates of Thiol- or Selenol-Amines and Antioxidant Vitamins

1. Agent Design

The present invention focuses on the antioxidant vitamins C and E, and the thiol or selenol agents, cyst(e)ine, cyst(e)amine, N-acetylcysteine, glutathione, WR-1065/WR-33278, selenocyst(e)ine, and selenocyst(e)amine. This represents a minimum of 24 combinations of the two classes. It will be appreciated by those skilled in the art that other antioxidants can be conjugated to these thiol- or selenol-containing compounds.

2. Chemical Synthesis

The schemes below summarize potential approaches using cysteamine for illustrative purposes. Many permutations are available.

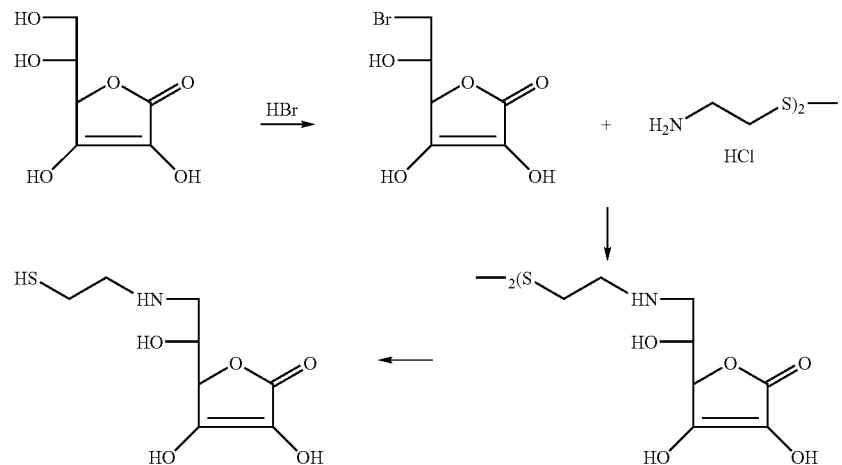

Growth curves were generated for the bacteria in the absence of any treatment to provide experience with basic handling as well as important baseline information. The radiation dose response of the system was investigated irradiating bacterial cultures in a Shepherd Mark I $^{137}$Cs irradiator over a dose range of 0 to 1 kGy. The dose-response curves are linear and reproducible from day to day. From these data, a radiation dose of 0.6 kGy was chosen for the initial radioprotection experiments in order to achieve approximately a 0.1% survival in the unprotected cultures, a common target for these types of studies.

The toxicity of the compounds of interest in this system was explored. Administering the 2-oxocysteamine prodrug completely eliminated the profound toxicity observed with cysteamine itself; neither WR-1065 nor its 2-oxo prodrug produced any toxicity in this assay.

Radioprotection experiments were also conducted in the bacterial system. For these experiments, the bacteria were grown to log phase and then treated with the agent of choice (parent, prodrug, or positive control) for 1 hour before irradiation at 0.6 kGy. Surviving fraction compared to that seen in control (untreated) cells, which were not irradiated, was then IV. Modified Prodrugs of L-Cysteine or L-Selenocysteine 1. Agent Design These prodrugs possess a modified carboxyl group compared to unmodified prodrugs of L-cysteine and L-selenocysteine. The purpose of the modification is to reduce the hydrophilicity of the prodrugs and improve their cellular uptake and retention in the body. The modifications include converting the carboxyl group to an ester or amide functionality.

In one aspect, the compound has the formula

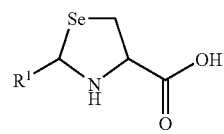

wherein $R^1$ is hydrogen, an alkyl group, an aryl group, a cycloalkyl group, an alkenyl group, an alkynyl group, an aralkyl group, or =O, or the pharmaceutically acceptable salt or ester thereof. In one aspect, $R^1$ is a cycloalkyl group such as, for example, cyclopropyl, cyclobutyl, cyclopentyl, cyclohexyl, cycloheptyl, or cyclooctyl. In another aspect, $R^1$ is a phenyl group substituted with one or more hydroxyl or alkoxy groups. In a further aspect, $R^1$ is 2-hydroxyphenyl.

2. Chemical Synthesis

Ester prodrugs were prepared beginning with commercially available L-cysteine methyl or ethyl ester. The ester is combined with an equimolar amount of carbonyl donor, i.e., acetaldehyde, the aldose monosaccharide, D-ribose, or phenyl chloroformate. The amide prodrugs were prepared by the initial synthesis of L-cysteine amides (not commercially available) from L-cysteine and the appropriate amine, such as ammonia, methylamine, or dimethylamine. The synthesized L-cysteine amides were then reacted with an equimolar amount of carbonyl donor, i.e., acetaldehyde, the aldose monosaccharide, D-ribose, or phenyl chloroformate.

Modified prodrugs of L-selenocysteine can be constructed in an identical fashion. However, L-selenocysteine methyl or ethyl ester are prepared by the esterification of L-selenocysteine with methanol or ethanol because these compounds are not commercially available.

For example, the reaction of L-cysteine ethyl ester and D-ribose may be as follows;

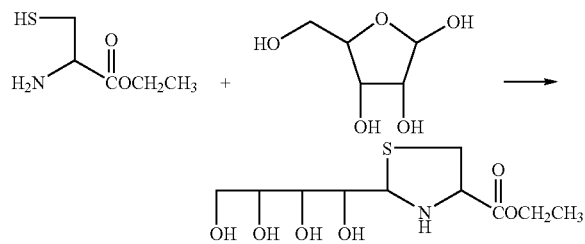

V. Selenazolidines: Modified Prodrugs of Selenocysteine and Selenocysteamine

1. Agent Design

Current selenium supplements rely on inorganic forms. While these forms have some value, they are considered more toxic than necessary, and are unlikely to be useful in cancer chemoprevention or in AIDS supplementation. Several organoselenium compounds, which appear to be less toxic in general than the inorganic forms, have been proposed for in vivo use, but the full potential of this strategy has not yet been realized. In general, however, it is very clear that the chemical form in which selenium is introduced consistently shows a marked influence on biological outcomes. Selenocysteine is an organic form that is present in the body and is now recognized as the 21st amino acid used in protein synthesis. Due to its differential metabolism, it represents the biochemically superior form in which to supply the body with selenium. Unfortunately, selenocysteine is chemically unstable and difficult to handle. Therefore, prodrug forms of the amino acid have been designed which represent chemically superior forms. Similar arguments hold for selenocysteamine as well.

2. Chemical Synthesis

Selenocysteine/selenocysteamine prodrugs can be synthesized by the chemical condensation of the selenolamine with a carbonyl donor. Alkyl or aryl aldehydes or ketones can be used, including simply donors such as acetaldehyde or benzaldehyde, or aldose or ketose mono- or di-saccharides. In addition, carbonyl donors such as phenyl chloroformate can be used to produce 2-oxo derivatives.

For example, the reaction of L-selenocysteine and phenyl chloroformate is illustrated.

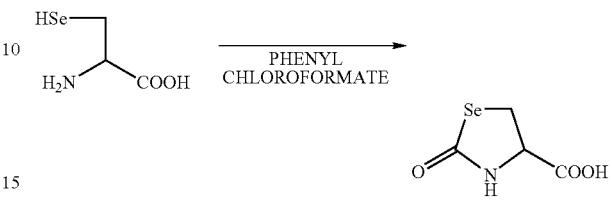

3. Examples

Three novel selenazolidines, 2-methyl-, 2-oxo- and 2-unsubstituted (i.e., selenaproline) selenazolidine-4[R]-carboxylic acid (MSCA, OSCA, and SCA respectively) that had been synthesized as prodrugs of selenocysteine were evaluated for their potential to act as cancer chemopreventive agents. [Se] and GPx activity were evaluated. The key results of the initial cancer chemoprevention study are summarized in Table 1. For the treatment regimen used in this four-month NNK lung tumor study, OSCA showed significant tumor reduction.

L-Selenocystine. At room temperature, selenium powder (3.0 g, 38 mmol) was suspended in water (10 mL). Sodium borohydride (3.0 g, 79 mmol) was dissolved in water (19 mL) and slowly added to the selenium suspension with stirring. Another equivalent of selenium powder (3.0 g, 38 mmol) was added to the reaction and the mixture was stirred for 15 min. The reaction mixture was placed briefly on a steam bath (1-2 min) to drive the reaction to completion. β-Chloro-L-alanine HCl (3.2 g, 20 mmol) was dissolved in water (20 mL) at pH 9 and added dropwise to the selenium solution over 2 h; stirring was continued overnight at 37° C. The reaction mixture was acidified to pH 2 and hydroxylamine hydrochloride (218 mg, 3.1 mmol) was added. CAUTION: Added safety precautions were implemented during the work up of this reaction due to the production of hydrogen selenide gas. The reaction vessel was sealed tightly to prevent release of $H_2Se$ into the air, and the exhaust was forced through two lead acetate traps, each containing 25 g lead acetate in 300 mL water, for 2 h. As an added precaution, a respirator rated for $H_2S$ was routinely used. Vacuum filtration was performed to remove elemental selenium, and the filtrate was adjusted to pH 6-6.5 and left to crystallize at 4° C. for 3-5 days. The yellowish-orange crystals were collected by vacuum filtration and redissolved in 1 M HCl (20 mL). Any remaining solids were removed by vacuum filtration. The filtrate was adjusted to pH 6-6.5 with and left to crystallize again for 3-5 days. The yellow crystals were collected by vacuum filtration and dried by vacuum overnight: 3.0 g, 9.0 mmol (90%). Mp 174-176° C. (d) (reported, lit.[27] 184-185° C.). TLC n-BuOH/ $H_2O$/acetic acid (3:2:1), $R_f$0.32. $^1H$ NMR ($D_2O$/NaOD, 500 MHz) δ 3.6 (dd, J=5, 7 Hz, 1H, H-α), 3.3 (dd, J=5, 12 Hz, 1H, H-β1), 3.2 (dd, J=7, 12 Hz, 1H, H-β2); $^{13}C$ NMR ($D_2O$/Na (OD, 125 MHz) δ 181.0(COOH), 56.3 (C-α), 35.8 (C-β); $^{77}Se$ NMR ($D_2O$/NaOD, 95.3 MHz) δ 288.1 IR (KBr) $v_{max}$ 3500, 3000 $cm^{-1}$. FABMS [$M^+$+1] m/z 336.9 ($^{80}Se$). $[δ]^{25}_{-}$ 29.0°(c 21.6; H, 3.63; N, 8.38. Found: C, 21.2; H, 3.57; N, 8.29.

2-Oxoselenazolidine-4(R)-carboxylic acid (OSCA). L-Selenocystine (0.25 g, 0.75 mmol) was suspended in an evacuated flask containing 0.05N NaOH (10 mL) and ethanol (3 mL). To the solution, sodium borohydride (0.1 g, 2.6 mmol) was added slowly over about 10 min. The yellow solution was stirred for an additional 20 min until it became colorless and then was placed in an ice bath. The pH was adjusted to 5-6. 1,1'-Carbonyldiimidazole (0.2 g, 1.2 mmol) was added over 30 min, and the reaction mixture was stirred for 1 h. If the reaction mixture became yellow again, the above reduction and carbonylation steps were repeated. The reaction mixture was acidified to pH 2 and extracted with ethyl acetate (3×15 mL). The combined ethyl acetate layers were washed with saturated NaCl solution (2×15 mL), dried over $MgSO_4$, then concentrated and dried under vacuum: 0.12 g, 0.62 mmol (41%). Mp 144-146° C. (d). TLC n-BuOH/$H_2O$/acetic acid (3:2:1), $R_f$ 0.65. $^1H$ NMR ($D_2$), 500 MHz) δ 4.5 (dd, J=6, 8 Hz, 1H, H-4), 3.8 (dd, J=8, 10 Hz, 1H, H-5a), 3.6 (dd, J=6, 10 Hz, 1H, H-5b); $^{13}C$ NMR ($D_2O$, 125 MHz) δ 178.7, 178.5 (COOH, C-2), 61.0 (C-4), 34.3 (C-5); $^{77}Se$ NMR ($D_2O$, 95.3 MHz) δ 1352.8 IR (KBr) $v_{max}$ 3300, 3000, 1700 $cm^{-1}$. FABMS [$M^+$+1] m/z 195.9 ($^{80}Se$). [$α^{25}$-67.9° (c 0.5, water). Anal. calcd for $C_4H_5NO_3Se$:C, 24.8; H, 2.60; N, 7.22. Found: C, 24.4; H, 2.72; N, 6.93.

2(R,S)-Methylselenazolidine-4(R)-carboxylic acid (MSCA). L-Selenocystine (0.13 g, 0.39 mmol) was suspended in an evacuated flask containing 0.05 N NaOH (5 mL) and ethanol (1.5 mL). Sodium borohydride (0.05 g, 1.3 mol) was added slowly over about 10 min. The reaction mixture was stirred for an additional 20 min until it changed to colorless and was then placed in an ice bath. The pH was adjusted to 5-6. Acetaldehyde (0.24 mL, 4.3 mmol) was added in 80 µL aliquots over 30 min, and the reaction mixture was stirred for 3 h. At that point, ethanol (20 mL) was added and the mixture was stored in the refrigerator overnight. The yellow precipitate (selenocystine by MS and NMR; data not shown) was filtered off, and the filtrate was dried under vacuum: 0.09 g, 0.47 mmol (60%). Mp 136-138° C. (d). $^1H$ NMR ($D_2O$, 400 MHz) δ diastereomer A 5.1 (q, J=7 Hz, 1H, H-2), 4.6 (t, J=7 Hz, 1H, H-4), 3.5-3.3 (m, 2H, H-5), 1.7 (d, J=7 Hz, 3H, $CH_3$); $^{13}C$ NMR ($D_2O$, 100 MHz) δ diastereomer A 171.7 (COOH), 66.4 (C-4), 50.7 (C-2), 24.2 (C-5), 18.8 ($CH_3$); diastereomer B 171.5 (COOH), 64.9 (C-4), 50.7(C-2), 24.2 (C-5), 21.1 ($CH_3$); $^{77}Se$ NMR ($D_2O$, 76.2 MHz) δ 320.2, 315.7 IR (KBr) $v_{max}$ 3250, 2900, 1690 $cm^{-1}$. FABMS [$M^+$+1] m/z 196.0 ($^{80}Se$). [$α$]$^{25}$-83.9 (c 0.5, water). Anal. calcd for $C_5H_9NO_2Se$. ½ $H_2O$: C, 29.6; H, 4.96; N, 6.90. Found: C, 29.4; H, 4.45; N, 6.81.

Linking efficacy to biochemical parameters and a mechanism was limited in the initial study by only two parameters, [Se] and GPx activity. The in-vivo effects of selenazolidine compounds were then evaluated using, in addition to GPx, glutathione S-transferases (GSTs), quinone oxidoreductases (NQORs), UDP-glucuronosyltransferases (UGTs), and microsomal epoxide hydrolase (mEH). To investigate transcriptional changes of these classes of enzymes, it was necessary to develop a battery of cDNA probes for use in Northern blot analysis of RNA extracted from treated animals (Table 2).

Whether the selenaproline compounds had the ability to up-regulate the transcription of Phase II and/or other "protective" enzymes was first evaluated following a single dose of each (Table 3). Only the Ugt genes showed statistically significant induction, and these were unique to OSCA. The experiment was repeated but with a 7-day treatment regimen (Table 4), the time period for which the compounds were given in the diet before NNK administration in the tumor experiment reported in Table 1. The significant increases in major mRNA transcripts detected by the Ugt1a1 and Ugt1a9 after one dose of OSCA remained evident with multiple doses, but the mRNA detected by the UGT1a6 probe did not. With multiple doses, SCA induced Ugt1a9, an mRNA that was not changed with a single dose. With multiple doses of OSCA, statistically significant increases in both GSTalpha and GSTmu transcripts were also evident. (Retrospective perusal of the single dose experiment, Table 3, showed that these mRNAs were most elevated with OSCA treatment). The elevation in the Gst-mu transcript was unique to multiple OSCA treatment. The elevation of the GST-alpha mRNA was also seen with SCA treatment. Microsomal epoxide hydrolase mRNA was robustly elevated by multiple doses of all three selenaproline compounds, an effect not anticipated from the single dose experiment where not even minor changes were apparent.

A kinetic thioredoxin reductase assay was developed using the aurothioglucose inhibitable fraction of NADPH-dependent DTNB (5,5' dithiobis(2-nitrobenzoic acid) reduction as the monitor. A kinetic UGT(p-nitrophenol) assay can be used as a monitor of multi-enzyme UGT activity, and a radiometric TLC assay capable of differentiating isozyme-selective activities is available. A fluorimetric 96-well format Cyp2a5-dependent coumarin hydroxyls assay had been developed for investigation of changes in NNK bioactivation.

Of the three selenaproline compounds evaluated, it was noted that the tumor-reducing OSCA had the highest calculated partition coefficient of the compounds evaluated, a parameter that could favor its diffusion into cells. Accordingly, additional compounds were synthesized with a range of partition coefficients (Table 6) and evaluated their ability to alter gene transcription following single (Table 7) and multiple (Table 8) doses. The new 2-(R,S)-substituted-4(R)-carboxylic acid derivatives involving 2-butyl, 2-cyclohexyl, 2-phenyl and 2-(2-hydroxyphenyl) were synthesized utilizing the reaction of selenocysteine and the appropriate carboxaldehyde. They were purified by crystallization from ethanol/acetonitrile mixtures and their molecular structures were verified by spectral methods of analysis ($^1HNMR$, $^{13}CNMR$, ESIMs and HRMS). Previous studies had shown the butyl derivative to be much more stable in aqueous solution than MSCA.

With a single dose (Table 7), ChSCA, which has a similar calculated partition coefficient to OSCA, produced elevations in the transcripts of Ugt1a1 and Ugt1a6, as was the case with OSCA. These two Ugt trasncripts were also elevated by PhOHSCA which has a very different partition coefficient from OSCA and PhSCA. This PhOHSCA effect is different from MSCA, a compound with a similar partition coefficient. Thus overall, Ugt transcript elevation appears to be unrelated to partition coefficient. The Ugt1a9 transcript appeared statistically elevated (against naive animals) by two of the four compounds, CnSCA and BSCA. Compared to the corn oil effect, PhOHSCA significantly reduced the expression of this transcript.

As with SCA, MSCA, and OSCA, none of the compounds showed hepatotoxicity (elevations in sALT) with multiple doses (Table 8). Many of the mRNA changes seen with a single dose were not sustained with multiple dosing. Changes in Ugt transcripts after multiple dosing were noticeably absent. Unique to BSCA among the four new compounds investigated was its ability to induce Gst-alpha, Gst-mu and GPx mRNAs. For the Gst-alpha transcripts, which appeared elevated by corn oil, the BSCA increase was much greater than the vehicle alone (8-fold versus 2-fold) and was statistically significant (p<0.05). BSCA shared with PhOHSCA the ability to elevate mEH mRNA. ChSCA and PHSCA failed to induce any mRNAs following 7 daily doses.

TABLE 1

The effect of selenaproline derivatives on lung tumor development
and hepatic and RBC parameters in a four-month feeding study.

| Parameter | Naive | NNK | NNK + SCA | NNK + MSCA | NNK + OSCA |
|---|---|---|---|---|---|
| NNK Tumors | 0 | 7.2 ± 0.6 | 6.7 ± 0.8 | 8.3 ± 0.9 | 4.5 ± 0.4* |
| Body wt gain (%) | 56.1 | 51.8 | 51.1 | 49.3 | 39.9* |
| Liver weight (g) | 1.20 ± 0.03 | 1.00 ± 0.03 | 1.18 ± 0.02* | 1.17 ± 0.02* | 1.02 ± 0.02 |
| Hepatic [Se] (μg/g tissue) | 1.86 ± 0.16 | 2.03 ± 0.12 | 2.43 ± 0.11 | 2.97 ± 0.23* | 2.92 ± 0.22* |
| Hepatic (tButylOOH) GPx | 337 ± 19 | 375 ± 17 | 409 ± 46 | 564 ± 46* | 518 ± 59* |
| RBC [Se] | 11.78 ± 0.76 | 12.73 ± 0.84 | 17.94 ± 1.52* | 13.00 ± 1.14 | 19.46 ± 0.95* |
| RBC (tButylOOH) GPx | 181 | 188 ± 6 | 253 ± 33* | 220 ± 32 | 281 ± 24* |

*significantly different (p < 0.05) from the NNK group.

Where indicated, mice (16 g) were given diets fortified with SCA, MSCA or OSCA (15 ppm Se) for 1 week prior to NNK (10 umol, ip). Two other groups received the unmodified AIN-76A diet, with and without NNK administration. All groups were maintained on their pretreatment diet until the animals were sacrificed after 16 weeks. Liver GPx activity is expressed as μmol NADPH oxidized [in regenerating GSH]/min/mg 10,000 g×20 min supernatant protein; RBC activity as μmol/min/mg RBC lysate hemoglobin.

TABLE 2

Northern Blot Probes

| Probe | Origin | Cross homology |
|---|---|---|
| alpha class GSTs | +1 to +700 of Gstα2 (Accession: BC061134) | 97% with Gstα1 (NM 008181), 76% with Gstα3, (NM 010356), 66% with Gstα4 (NM 010357); <45% with GSTμ forms. |
| mu class GST | +200 to +784 Gstμ1 (Accession NM_010358) | 86-91% with Gstμ2 (NM 008183), Gstμ3 (NM 010359), Gstμ5 (J04696); and Gstμ6 (BC031818), 66% with Gstμ4 (NM 026764) |
| UGT1a1 | +1 to +750 of rat UGT1A1 (Accession: U20551). | >88% cross species |
| Ugt 1 a6 | +9 to +765 of Ugt 1 a6 (Accession: U09930) | |
| Ugt 1 a9. | +1 to +750 of Ugt 1 a9 (Accession: BC026561) | |
| Ugt2b5 | 1 to 804 of Ugt2b5 (Accession; X06358) | |
| GPx | +1 to +670 of Gpx 1 (Accession: NM_008160), | 71% with Gpx2 (NM 030677) <65% with Gpx3-Gpx7. |
| mEH | +107 to +1531 of rat mEH (Accession: M26125) | >88% cross species |
| NQOR | +1 to +1480 of NQOR1 (Accession: U12961) | |

TABLE 3

The effect of 1 dose (ip) of selenaproline derivatives
on 'protective' enzyme mRNAs

| mRNA | SCA | MSCA | OSCA |
|---|---|---|---|
| Ugt1a1 | 1.03 ± 0.18 | 1.07 ± 0.11 | 2.41 ± 0.76* |
| Ugt1a6 | 1.01 ± 0.29 | 1.21 ± 0.28 | 1.74 ± 0.57* |
| Ugt1a9 | 1.35 ± 0.50 | 1.47 ± 0.18 | 1.88 ± 0.51* |

TABLE 3-continued

The effect of 1 dose (ip) of selenaproline derivatives
on 'protective' enzyme mRNAs

| mRNA | SCA | MSCA | OSCA |
|---|---|---|---|
| Gst-alpha | 1.15 ± 0.28 | 1.00 ± 0.19 | 1.61 ± 0.53 |
| Gst-mu | 1.28 ± 0.09 | 1.07 ± 0.57 | 1.38 ± 0.33 |
| mEH | 1.36 ± 0.40 | 1.06 ± 0.12 | 0.88 ± 0.19 |
| GPx (1.5 kb) | 1.12 ± 0.04 | 1.65 ± 0.27 | 0.80 ± 0.22 |

*significantly different (p < 0.05) from naive animals. Mice were treated with equi-selenium doses (1.25 mg Se/kg, ip) of each agent. Liver RNA was extracted 24 hours after dosing and mRNAs analyzed by northern blotting using P-32 labeled probes and quantified by densitometric scanning of autoradiographs. Several probes showed minor bands in addition to the major bands that were quantified. Each mRNA of interest was normalized to same-sample simultaneously-run cyclophilin mRNA. The results from 3-4 individual animals were quantified and the results are reported as mean fold change from naive ± SEM

TABLE 4

The effect of 7 daily doses (ip) of selenaproline
derivatives on 'protective' enzyme mRNAs

| Parameter | SCA | MSCA | OSCA |
|---|---|---|---|
| sALT | 28.9 ± 3.8 | 37.0 ± 4.5 | 47.6 ± 11.3 |
| Ugt1a1 | 2.25 ± 0.25 | 1.15 ± 0.09 | 2.62 ± 0.94* |
| Ugt1a6 | 1.01 ± 0.07 | 1.02 ± 0.15 | 0.63 ± 0.17 |
| Ugt1a9 | 2.06 ± 0.01* | 1.22 ± 0.29 | 2.22 ± 0.24* |
| Gst-alpha | 1.84 ± 0.99* | 1.18 ± 0.33 | 3.35 ± 2.75* |
| Gst-mu | 0.58 ± 0.11 | 1.65 ± 0.18 | 3.09 ± 0.71 |
| mEH | 3.25 ± 1.80* | 3.35 ± 1.21* | 2.91 ± 1.48* |
| GPx | 1.55 ± 0.76 | 1.43 ± 0.35 | 1.13 + 0.39 |

*significantly different (p < 0.05) from naive animals. Mice were treated with equi-selenium doses (1.25 mg Se/kg, ip) of each agent. Liver RNA was extracted 24 hours after the last dose and mRNAs analyzed by northern blotting using P-32 labeled probes and quantified by densitometric scanning of autoradiographs. Several probes showed minor bands in addition to the major bands that were quantified. Each mRNA of interest was normalized to same-sample simultaneously-run cyclophilin mRNA.The results from 3 individual animals were quantified and the results are reported as mean fold change from naive ± SEM The sALT value in untreated mice was 42.6 ± 7.6. No treatment resulted in significant hepatotoxicity.

TABLE 5

The effect of 7 daily doses (ip) of selenaproline
derivatives on hepatic cytosolic enzyme activities

| Activity* | Naive | SCA | MSCA | OSCA |
|---|---|---|---|---|
| GST (CDNB) | 5248 ± 503 | 6576 ± 595 | 6948 ± 502 | 6887 ± 1142 |
| GPx (H202) | 894 ± 36 | 862 ± 81 | 944 ± 32 | 880 ± 72 |

*nmol/mg cytosol (100,000 g supernatant) protein/min.

TABLE 6

Calculated partition coefficients (Clog P) of selenaproline derivatives

| | | |
|---|---|---|
| selenazolidine-4-carboxylic acid | SCA | −3.062 |
| 2-methyl-SCA | MSCA | −2.543 |
| 2-(2-hydroxyphenyl)-SCA | PhOHSCA | −2.551 |
| 2-phenyl-SCAS | PhSCA | −1.884 |
| 2-n-butyl-SCA | BSCA | −0.956 |
| 2-oxo-SCA | OSCA | −0.529 |
| 2-cyclohexyl-SCA | ChSCA | −0.512 |

TABLE 7

The effect of 1 dose (ip) of additional selenaproline derivatives on 'protective' enzyme mRNAs

| mRNA | ChSCA + co | BSCA + co | PhSCA + co | PhOHSCA + co | corn oil (co) |
|---|---|---|---|---|---|
| Ugt1a1 | 1.77 ± 0.23* | 0.83 ± 0.28 | 1.41 ± 0.30 | 2.47 ± 0.26* | 1.09 ± 0.29 |
| Ugt1a6 | 2.07 ± 0.46* | 1.95 ± 0.21 | 1.78 ± 0.54 | 2.93 ± 0.52* | 1.14 ± 0.19 |
| Ugt1a9 | 3.04 ± 0.55* | 3.25 ± 1.41* | 2.14 ± 0.54 | 1.65 ± 0.32 | 3.21 ± 0.83* |
| Gst-alpha | 1.73 ± 0.20 | 1.39 ± 0.05 | 0.63 ± 0.14 | 1.49 ± 0.22 | 1.31 ± 0.17 |
| Gst-mu | 1.20 ± 0.15 | 1.58 ± 0.46 | 0.74 ± 0.16 | 1.18 ± 0.32 | 1.04 ± 0.25 |
| mEH | 1.34 ± 0.41 | 0.69 ± 0.19 | 0.98 ± 0.27 | 1.38 ± 0.48 | 0.56 ± 0.43 |
| GPx | 1.20 ± 0.15 | 1.58 ± 0.46 | 0.74 ± 0.16 | 118 ± 0.32 | 1.04 ± 0.25 |

*significantly different ($p < 0.05$) from naive animals. Mice were treated with equi-selenium doses (1.25 mg Se/kg, ip) of each agent in corn oil. Liver RNA was extracted 24 hours after dosing and mRNAs analyzed by northern blotting using P-32 labeled probes and quantified by densitometric scanning of autoradiographs. Several probes showed minor bands in addition to the major bands that were quantified. Each mRNA of interest was normalized to same-sample simultaneously-run cyclophilin mRNA. The results from 3-4 individual animals were quantified and the results are reported as mean fold change from naive ± SEM

TABLE 8

The effect of 7 daily doses (ip) of additional selenaproline derivatives on 'protective' enzyme mRNAs

| Parameter | ChSCA + co | BSCA + co | PhSCA + co | PhOHSCA + co | corn oil (co) |
|---|---|---|---|---|---|
| sALT | 40.0 ± 1.7 | 37.1 ± 2.7 | 37.3 ± 1.4 | 42.4 ± 3.0 | 45.7 ± 5.1 |
| Ugt1a1 | 1.20 ± 0.17 | 1.21 ± 0.26 | 1.32 ± 0.12 | 0.77 ± .04 | 1.31 ± 0.32 |
| Ugt 1 a6 | 1.22 ± 0.17 | 1.84 ± 0.54 | 0.96 ± 0.04 | 0.99 ± 0.14 | 1.01 ± 0.10 |
| Ugt 1 a9 | 1.16 ± 0.13 | 1.69 ± 0.35 | 0.83 ± 0.08 | 1.06 ± .14 | 0.91 ± 0.08 |
| Gst-alpha | 1.99 ± 0.77 | 8.05 ± 2.62* | 2.29 ± 0.68 | 1.91 ± 0.71 | 1.95 ± 0.68 |
| Gst-mu | 1.32 ± 0.21 | 4.39 ± 1.77* | 1.01 ± 0.27 | 1.54 ± 0.23 | 0.98 ± 0.23 |
| mEH | 1.31 ± 0.19 | 2.70 ± 0.50* | 0.80 ± 0.15 | 3.17 ± 0.62* | 0.99 ± 0.09 |
| GPx | 2.26 ± 0.66 | 2.87 ± 1.03* | 1.46 ± 0.35 | 1.51 ± 0.50 | 2.22 ± 0.95 |

*significantly different ($p < 0.05$) from naive animals. Mice were treated with equi-selenium doses (1.25 mg Se/kg, 1p) of each agent. Liver RNA was extracted 24 hours after the last dose and mRNAs analyzed by northern blotting using P-32 labeled probes and quantified by densitometric scanning of autoradiographs. Several probes showed minor bands in addition to the major bands that were quantified. Each mRNA of interest was normalized to same-sample simultaneously-run cyclophilin mRNA. The results from 3-4 individual animals were quantified and the results are reported as mean fold change from naive ± SEM The sALT value in untreated mice was 37.5 ± 2.9. No treatment resulted in significant hepatotoxicity.

VI Methods

1. Administration

The compounds of the invention defined above, including the pharmacologically acceptable esters, amides or salts thereof, are useful for reducing the unwanted side effects of chemo- or radiotherapy of cancer, improving cardiovascular function, preventing mutagenesis, preventing the initiation and/or progression of cancer, treating cancer, reducing toxic consequences of planned or unplanned radiation or chemical exposures, slowing affects of the aging process, and treating or preventing cataract formation, for example.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that may be used in conjunction with the preparation of formulations of the inventive compounds and which is incorporated by reference herein.

The compounds may be administered orally, parenterally (e.g., intravenously), by intramuscular injection, by intraperitoneal injection, topically, transdermally, or the like, although oral administration is preferred. The amount of active compound administered will, of course, be dependent on the subject being treated, the subject's weight, the manner of administration and the judgement of the prescribing physician. Generally, however, dosage will approximate that which is typical for the administration of thiols, and will preferably be in the range of about 1 μg/kg/day to 100 mg/kg/day. The USDA has set out guidelines for the administration of selenium to humans (Institute of Medicine, Food and Nutrition Board. Dietary Reference Intakes: Vitamin C, Vitamin E, Selenium, and Carotenoids. National Academy Press, Washington, D.C., 2000, herein incorporated in its entirety for its teaching regarding dosages and methods of administration.) Generally, these guidelines are applicable to the compounds disclosed herein.

The administration of thio-, selenol, and related compounds is well known in the art. The compositions described herein have the same effects as known thio- and selenol compounds, without the toxic side effects. Therefore, the mode of administration and dosage of the compounds claimed herein are generally similar if not identical to the modes of administration and dosages of the compounds known in the art. Therefore, one skilled in the art would be apprised of how to administer the compounds of the invention as well as the effective amounts of these compounds.

For example, El-Bayoumy et al. (J. Cell. Biochem., Supp. 22:92-100, 1995, herein incorporated in its entirety for its teaching concerning dosages and methods of administration) discloses cancer prevention by organoselenium compounds such as 1,4-phenylenebis(methylene)selenocyanate (p-XSC). In Table 1 of El-Bayoumy, p-XSC is given in concentrations of 5, 10, and 15 ppm. Each consecutively higher dose shows a marked decrease in total tumor yield. El-Bayoumy also discusses dosages for selenium and notes that levels above 5 ppm are toxic (p. 93) and uses a dosage of 3 ppm as a control (Table 1). El-Bayoumy also teaches the "chemopreventative index," which is calculated by obtaining the ratio of maximum tolerable dose to the effective dose which produced approximately 50% inhibition in total tumor yield. This formula allows for one of ordinary skill in the art to calculate an effective dosage to inhibit tumor growth. El-Bayoumy also teaches that effective modes of administration include diet or drinking water. Therefore, one of ordinary skill in the art would have been able to easily assess effective dosages and routes of administration for the compositions disclosed herein.

Furthermore, the administration of thio-compounds and selenium to treat those conditions recited herein was well known in the art. The compounds disclosed herein are derivatives and prodrugs of compounds known in the art for reducing the unwanted side effects of chemo- or radiotherapy of cancer, improving cardiovascular function, preventing mutagenesis, preventing the initiation and/or progression of cancer, reducing toxic consequences of planned or unplanned radiation or chemical exposures, slowing the aging process, and preventing cataract formation.

While the selenium compounds in the present invention can treat these maladies, they have the added benefit of being less toxic than their corresponding compounds known in the art. Furthermore, the mode of administration and dosage of the selenium compounds claimed herein are generally similar if not identical to the modes of administration and dosages of the thiol compounds known in the art. Therefore, one skilled in the art would have been apprised of how to administer the compounds of the invention as well as the effective amounts of these compounds.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

For topical administration, liquids, suspension, lotions, creams, gels or the like may be used as long as the active compound can be delivered to the surface of the skin.

2. Methods of Treatment

The compounds disclosed herein are useful in reducing unwanted side effects of chemo- or radiotherapy of cancer. Treatment for cancer usually involves a combination of surgery and chemotherapy. Most drugs used in chemotherapy interfere with the growth of cancer cells. These drugs also affect the health of normal cells, often causing problems including anemia, hair loss, diarrhea, increased susceptibility to infections, and painful sores in the mouth. Other chemotherapy side effects are unusual tiredness, nausea, vomiting, appetite loss, kidney damage, and general feelings of illness (malaise).

Chemotherapy generates free radicals, a group of highly reactive molecules. Chemotherapy reduces the amount of selenium in the body, and a deficiency of selenium is associated with more kidney damage from chemotherapy. Selenium has the ability to bind with certain heavy metals including platinum (a component of cisplatin), resulting in a less toxic compound. Selenium can also help protect the body from developing cancer.

Sieja et al. (Gynecologic Oncology (2004;93:320-7) examined the effect of selenium as part of an antioxidant formula on the side effects of chemotherapy. Women with ovarian cancer who received selenium had significantly higher amounts of glutathione peroxidase in their red blood cells than the women in the group not receiving selenium, showing improved antioxidant activity as a result of selenium supplementation. The selenium-treated group also had significantly more neutrophils, a type of white blood cell responsible for fighting bacterial infections. This finding is important as infections are more likely in people undergoing chemotherapy, and in cancer patients in general. The group receiving selenium also experienced significantly less nausea, vomiting, abdominal pain, mouth sores, hair loss, weakness, malaise, and loss of appetite as a result of chemotherapy than the group without selenium.

The compounds disclosed herein are also useful in treating disorders associated with radiation therapy, or radiotherapy, such as, but not limited to, lymphedema. Lymphedema is a complication of radiation treatment for cancer. Symptoms include swelling of the limb or other parts of the body, and decreased mobility and a sense of heaviness in the affected area. If untreated, lymphedema can lead to cellulitis, chronic ulceration, and tissue necrosis. Micke O, et al. (Radiat Oncol Biol Phys 2003;56:40-49.) showed statistically significant improvement in patients with lymphedema treated with selenium.

Also in regard to reducing unwanted side effects of chemo- or radiotherapy of cancer, Tamba et al. (Z Naturforsch, 44:857-62, 1989, herein incorporated in its entirety for its teaching of reducing unwanted side effects of chemotherapy or radiation therapy) discloses thiols such as thiyl radicals derived from glutathione, cysteine, penicillamine, and 2-mercaptoethanol. Tamba et al. discloses "The importance of sulphur compounds as modifiers of radiation response dates almost 40 years ago, when it was observed that the presence of some exogenous thiols at the time of irradiation resulted in protection of biological systems in vitro as well as of animals in vivo. Numerous compounds with radioprotective potential, mainly sulfur containing, have since been designed, synthesized, and tested in vitro and in vivo systems."

Yarbo et al. (Sem. Oncol, 18(1):48-58, Supp. 2, 1991, herein incorporated by reference in its entirety for its teaching concerning cancer chemotherapy) disclose that sulfur-containing nucleophiles such as sodium thiosulfate are chemoprotectants for cancer chemotherapy. Yarbo also discloses that several other thiol-based compounds have shown activity in preventing cisplatin-induced toxicities. These include the experimental aminothiol WR-2721, the disulfide metal chelator diethyldithiocarbamate (DDTC), mesna, N-acetylcysteine, and thiourea. While some of these agents have only been evaluated in animal models (mesna, thiourea), DDTC has been found to be an effective chemoprotectant for the kidney in patients receiving either cisplatin or carboplatin. Yarbo goes on to disclose effective dosages for chemoprotection. Therefore, one of ordinary skill in the art would be apprised of how to administer the selenium compounds of the invention as well as the effective amounts of these compounds as chemo- and radioprotectants based upon what was well known in the art with respect to the administration of thiol compounds.

Also disclosed are methods of reducing toxic insult in a mammal, comprising administering to the mammal a compound disclosed herein. Bohm et al. (Cancer Res. 11:1613-1616, 1991, herein incorporated by reference in its entirety for its teaching concerning reduction of toxicity) shows that glutathione protects against cisplatin-induced renal toxicity without reducing the antitumor activity of the cytotoxic agent, along with effective dosages and methods of administration.

Also disclosed are methods of improving cardiovascular function comprising administering to the mammal a compound disclosed herein. Such improvement was demonstrated by Boucher et al. (Nutrition. 1995 September-October; 11(5 Suppl):708-11.) It was shown that selenium supplementation significantly increased the activity of cardiac mitochondrial glutathione peroxidase (GPx) in ADR-treated rats; selenium supplementation reduced myocardial malondialdehyde content in ADR-treated rats; and ADR treatment significantly increased the degree of reperfusion-induced structural alterations to sarcomeres compared to untreated hearts. This study demonstrated that selenium supplementation is able to limit ADR cardiotoxicity in isolated rat hearts submitted to a sequence of ischemia/reperfusion.

Steare et al. (J Mol Cell Cardiol 27:65-74, 1995, herein incorporated by reference in its entirety for its teaching regarding cardiovascular function) discloses that reactive oxygen species (free radicals) are generated during ischemia-reperfusion of the myocardium (heart), and can contribute to the pathophysiology of the heart. Steare et al. reviews the role of endogenous antioxidant systems in protection of the myocardium against ischemia-reperfusion and discusses the evidence that alterations in endogenous antioxidant status can provide protection of the heart to reversible and lethal cellular injury. Steare et al. shows the role of glutathione in the defense against the "oxidant stress of ischemia-reperfusion injury." Also discussed is that cellular levels of glutathione can be increased by administering glutathione itself or cysteine precursors. Therefore, based on the disclosure in Steare et al. for administering thiol compounds for preventing damage to the myocardium, one of ordinary skill in the art would be apprised of how to administer the selenium compounds of the invention as well as the effective amounts of these compounds to improve cardiovascular function.

Also disclosed are methods of preventing mutagenesis comprising administering to the mammal a compound disclosed herein. Diamond et al. (Mutat Res. September 1996; 23;356(2):147-54) showed inhibition of radiation-induced mutagenesis by the combined effects of selenium and the aminothiol WR-1065. Furthermore, mutagenesis is known to be caused by free radical damage, and as disclosed herein, selenium is known to counteract free radicals, thereby preventing mutagenesis.

Also disclosed are methods of slowing the aging process comprising administering to the mammal a compound disclosed herein. The antioxidant properties of selenoproteins help prevent cellular damage from free radicals. Free radicals are natural by-products of oxygen metabolism, and are associated with aging. Bezlepkin et al. (Mech. Aging Devel. 92:227-234, 1996, herein incorporated in its entirety for its teaching concerning slowing the aging process) teaches one of ordinary skill in the art that there is abundant evidence that the lesions in DNA, proteins and lipids and their accumulation with age can be responsible for cancer and various pathologies, and that this occurrence is caused by oxidative damage. Bezlepkin et al. show that selenium can reduce oxidative damage in vivo and, therefore, prevent the initiation and progression of cancer as well as reduce toxic consequences of radiation or chemical exposures, which cause oxidation.

Also disclosed are methods of preventing the initiation and/or progression of cancer, as well as treating cancer, comprising administering to the mammal a compound disclosed herein. Epidemiological studies have shown that an increased incidence of cancer can be associated with low serum selenium levels (Brock et al. Journal National Cancer Inst. Vol. 83:292-93; Clark et al, Archives of Env. Health, Vol. 46:37-42, Yoshizawa et al. Journal National Cancer Inst. Vol. 90:1219-24)) Clinical trials have shown that supplemental selenium reduced the incidence and mortality of several types of human cancers, including gastric cardia, esophageal (Blot et al., Journal National Cancer Inst. Vol. 85:1483-92; Taylor et al. Can. Res. Vol. 54:2029s-31s) liver (Yu et al. Biol. Trace Element Res. Vol. 29:289-94), and prostate cancer (Clark et al. JAMA, Vol. 276:1957-63; Clark et al. British Jnl. Urol. Vol. 81:730-34). In addition, selenium compounds have been shown to have antitumorigenic acitivities in vivo (Ip et al., Cancer Res. Vol. 60:2882-6; Schrauzer et al., Biol. Trace Element Res. Vol. 33:51-62: Reddy et al., Anticancer Res. Vol. 16:1123-1127).

Examples of cancer contemplated herein include, but are not limited to, lymphoma (Hodgkins and non-Hodgkins) B-cell lymphoma, T-cell lymphoma, leukemia such as myeloid leukemia and other types of leukemia, mycosis fungoide, carcinoma, adenocarcinoma, sarcoma, glioma, blastoma, neuroblastoma, plasmacytoma, histiocytoma, melanoma, adenoma, hypoxic tumour, myeloma, AIDS-related lymphoma or AIDS-related sarcoma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, head and neck carcinoma, hematopoietic cancer, testicular cancer, colo-rectal cancer, prostatic cancer, and pancreatic cancer.

Crary et al. (Med. Hypotheses 13:77-98, 1994, herein incorporated by reference in its entirety for its teaching concerning immunostimulant, anti-inflammatory, and anti-carcinogenic effects), disclose that "high but well tolerated doses of . . . selenium . . . have significant immunostimulant, anti-inflammatory, and anti-carcinogenic effects which are well documented in the existing biomedical literature. In addition, these antioxidants help to protect the structural integrity of ischemic or hypoxic tissues, and may have useful anti-thrombotic actions as well." Crary also states that selenium is the most potent broad-spectrum anti-carcinogenic agent that has yet been discovered. When added to food or water at 1-4 ppm, selenium has offered protection against a wide variety of carcinogens in animal models of carcinogenesis. Supplementary selenium has reduced the incidence of liver cancer in animals treated with AAF, or 3MeDAB, or colon cancer induced with DMH or MAM, of skin papillomas induced with DMBA, BP, and MCA, and of mammary tumors induced with DMBA . . . Supplementary selenium has also substantially reduced the incidence of incidence of 'spontaneous' mammary tumors in C3H mice; in one such study, a 10% life-long incidence of mammary tumors in selenium-treated mice contrasted with an 82% incidence in untreated controls.

Also disclosed are methods of treating or preventing cataract formation in a mammal comprising administering to the mammal a compound disclosed herein. Oxidative damage to the lens of the eye with increase in age is a major cause of cataract formation. Specifically, glutathione depletion has been implicated in the etiology of this eye disorder. Cai et al. (Biomed. Environ. Sci, 7:109-115, 1994, herein incorporated by reference in its entirety for its teaching regarding cataracts) discloses that selenium deficiency can be involved in the occurrence of cataracts. "The results showed that the decrease of antioxidative capability in the lenses of [selenium deficient] . . . rats accelerated the lipid peroxidation and generation of free radicals." It also discloses that it has been known in the art since 1971 that selenium concentration in the lens of patients suffering from cataract decreased ⅙ in the normal lens. Therefore, one of ordinary skill in the art would be apprised of how to administer the selenium compounds of the invention to prevent cataract formation, based on the teachings in the art.

Also disclosed are methods of reducing toxic consequences of planned or unplanned radiation or chemical exposures comprising administering to the mammal a compound disclosed herein. Ionizing radiation (IR) remains a main stream therapy for cancer, since it controls both primary and metastatic cancer without significant systemic damage. However, radiation therapy does cause IR-induced local damage of normal tissue (radiation toxicity), leading to a temporary or persistent impairment of irradiated tissues, which lowers the life quality of cancer patients. Some severe side effects can even result in the discontinuation of the life-saving radiation therapy (Johansen et al. Radiother Oncol. 40: 101-9 (1996), Niemierko et al. Int J Radiat Oncol Biol Phys. 25: 135-45, 1993., Wiess et al. Toxicology 15;189(1-2):1-20 (July 2003), Goiten et al. Cancer 55: 2234-9 (1985)). Radiation damage can also occur by exposure to nuclear radiation, or exposure to a weapon that causes radiation. Kumar et al. (Pharm. Ther. 39:301-309, 1988, herein incorporated in its entirety for its teaching concerning radioprotection) disclose that glutathione affords radioprotection.

A long-term experiment in 400 rats exposed to radiation following the Chernobyl pattern showed that a selenium-enriched diet started after exposure caused a longer average lifespan and a 1.5-3.5 fold decrease of leukemias and other malignancies, e.g. breast, thyroid and lung cancers, etc., at late times. Selenium was first demonstrated to provide protection against late effects which is equivalent to a whole-body dose reduction by 1.4 Sv (140 rem). (Nutrition Research 1996; 16 (3): 505-516).

Also disclosed are methods of treating or preventing diabetes comprising administering to the mammal a compound disclosed herein. Selenium has been reported to mimic the action of insulin. Studies have shown that selenium mediates a number of insulin-like actions such as stimulating glucose uptake and regulating metabolic processes including glycolysis, gluconeogenesis, fatty acid synthesis and the pentose phosphate pathway.

It has been reported that these actions are mediated through the activation of key proteins involved in the insulin-signal cascade. Selenium is also reported to play a role in reducing the oxidative stress associated with diabetes (Stapleton, S. R. (2000) Cell Mol Life Sci. 57(13-14):1874-9), thereby retarding the progression of the secondary complications of diabetes such as neuropathy, retinopathy and cataracts. Low selenium status has been associated with the incidence of arthritis. Studies show the beneficial role of selenium as a free radical that delays the progression of this condition.

Also disclosed are methods of reducing inflammation in a subject comprising administering to the subject a compound disclosed herein. Inflammation has shown to be treatable by the administration of selenium compounds (Leyck et al., Agents Actions. June 1990;30(3-4):426-31.) "Inflammatory disease" is defined as any disease state associated with inflammation. The inflammation can be associated with an inflammatory disease. Examples of inflammatory disease include, but are not limited to, asthma, systemic lupus erythematosus, rheumatoid arthritis, reactive arthritis, spondyarthritis, systemic vasculitis, insulin dependent diabetes mellitus, multiple sclerosis, experimental allergic encephalomyelitis, Sjogren's syndrome, graft versus host disease, inflammatory bowel disease including Crohn's disease, ulcerative colitis, and scleroderma. Inflammatory diseases also includes autoimmune diseases such as myasthenia gravis, Guillain-Barré disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, multiple sclerosis, vitiligo, ankylosing spondylitis, Pemphigus vulgaris, psoriasis, and dermatitis herpetiformis.

Inflammation can be associated with a number of different diseases and disorders. Examples of inflammation include, but are not limited to, inflammation associated with hepatitis, inflammation associated with the lungs, and inflammation associated with an infectious process. Inflammation can also be associated with liver toxicity, which can be associated in turn with cancer therapy, such as apoptosis induction or chemotherapy, or a combination of the two, for example.

When the inflammation is associated with an infectious process, the infectious process can be associated with a viral infection. Examples of viral infections include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian Immunodeficiency virus, Human Immunodeficiency virus type-1, and Human Immunodeficiency virus type-2.

The infectious process can also be associated with a bacterial infection. Examples of bacterial infections include, but are not limited to, *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

The infectious process can also be associated with a parasitic infection. Examples of parasitic infections include, but are not limited to, *Toxoplasma gondii, Plasmodium* species such as *Plasmodium falciparum, Plasmodium vivax, Plasmodium malariae*, and other *Plasmodium* species, *Trypanosoma brucei, Trypanosoma cruzi, Leishmania* species such as *Leishmania major, Schistosoma* such as *Schistosoma mansoni* and other *Shistosoma* species, and *Entamoeba histolytica*.

The infectious process can also be associated with a fungal infection. Examples of fungal infections include, but are not limited to, *Candida albicans, Cryptococcus neoformans, Histoplama capsulatum, Aspergillusfumigatus, Coccidiodes immitis, Paracoccidiodes brasiliensis, Blastomyces dermitidis, Pneomocystis carnii, Penicillium marneffi*, and *Alternaria alternata*.

The inflammation can be associated with an inflammatory disease. Examples of inflammatory disease include, but are not limited to, asthma, systemic lupus erythematosus, rheumatoid arthritis, reactive arthritis, spondyarthritis, systemic vasculitis, insulin dependent diabetes mellitus, multiple sclerosis, experimental allergic encephalomyelitis, Sjogren's syndrome, graft versus host disease, inflammatory bowel disease including Crohn's disease, ulcerative colitis, and scleroderma. Inflammatory diseases also includes autoimmune diseases such as myasthenia gravis, Guillain-Barré disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, multiple sclerosis, vitiligo, ankylosing spondylitis, Pemphigus vulgaris, psoriasis, and dermatitis herpetiformis.

In addition to the diseases and disorders discusse above, low levels of selenium in HIV/AIDS sufferers have been linked to higher mortality. Low plasma selenium status has also been linked with senility and cognitive decline in the elderly and with Alzheimer's disease. Selenium supplementation was observed to reduce the severity of epileptic seizures in children. Selenium supplementation is also reported to improve confused and depressed mental states; mental fatigue and anxiety in adults. Selenium deficiency reduces the activities of the selenium-dependent antioxidant enzymes, leading to a number of functional disorders including skeletal/muscular dysfunction, cardiac dysfunction, hepatic degradation, increased capillary permeability, and pancreatic degeneration.

Throughout this application, various publications are referenced. The disclosures of these publications in their entireties are hereby incorporated by reference into this application.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the formula

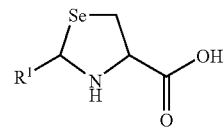

wherein $R^1$ is an alkenyl group, an alkynyl group, cyclopropyl, cyclobutyl, cyclopentyl, cyclohexyl, cycloheptyl, cyclooctyl, benzene, naphthalene, benzyl, or 2-hydroxyphenyl, or the pharmaceutically acceptable salt or ester thereof.

2. A compound having the formula

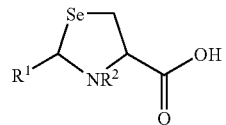

wherein $R^1$ is an alkyl group, an alkenyl group, an alkynyl group, cyclopropyl, cyclobutyl, cyclopentyl, cyclohexyl, cycloheptyl, cyclooctyl, benzene, naphthalene, benzyl, or 2-hydroxyphenyl, $R^2$ is an alkyl group, an alkenyl group, an alkynyl group, cyclopropyl, cyclobutyl, cyclopentyl, cyclohexyl, cycloheptyl, cyclooctyl, benzene, naphthalene, benzyl, or 2-hydroxyphenyl;

or the pharmaceutically acceptable salt or ester thereof.

\* \* \* \* \*